United States Patent
Glassman et al.

[11] Patent Number: 5,902,639
[45] Date of Patent: May 11, 1999

[54] METHOD OF FORMING BISMUTH-CONTAINING FILMS BY USING BISMUTH AMIDE COMPOUNDS

[75] Inventors: Timothy E. Glassman, Millshora, Oreg.; Gautam Bhandari, Danbury; Thomas H. Baum, New Fairfield, both of Conn.

[73] Assignee: Advanced Technology Materials, Inc, Danbury, Conn.

[21] Appl. No.: 08/828,566

[22] Filed: Mar. 31, 1997

[51] Int. Cl.$^6$ .................................................... C23C 16/00
[52] U.S. Cl. ................................... 427/248.1; 427/255.2; 427/255.1
[58] Field of Search ............................. 427/255.2, 255.1, 427/248.1

[56] References Cited

U.S. PATENT DOCUMENTS

| | | | |
|---|---|---|---|
| 4,702,791 | 10/1987 | Mimura et al. | 156/614 |
| 4,792,463 | 12/1988 | Okada et al. | 427/126.3 |
| 5,536,323 | 7/1996 | Kirlin et al. | 118/726 |

FOREIGN PATENT DOCUMENTS 62-294178  12/1987  Japan.

OTHER PUBLICATIONS

Communication, Synthesis and X–Ray Crystal Structure of a Homoleptic Bismuth Amide, William Clegg, et al., *Polyhedron* vol. 8, No. 12 pp. 1579–1580, 1989.

X–ray Crystal Structure of [$Bi(NMe_2)_3$], William Clegg, et al., *Inorg. Chem.*, 1991, 30, pp. 4680–4682.

*Primary Examiner*—Roy V. King
*Attorney, Agent, or Firm*—Steven J. Hultquist; Oliver A. M. Zitzmann

[57] ABSTRACT

A method of forming a bismuth-containing material layer on a substrate, comprising bubbler delivery or liquid delivery vaporization of a bismuth amide source reagent to form a bismuth-containing source vapor, and deposition on the substrate of bismuth from the bismuth-containing source vapor, to form the bismuth-containing material layer on the substrate. The bismuth amide source reagent may include a bismuth amide compound of the formula $BiL^1_x L^2_y (NR^1R_2)_z$ wherein: z is an integer of from 1 to 3; x+y+z=3; each of $L^1$ and $L^2$ is independently selected from $C_1$–$C_4$ alkyl, $C_1$14 $C_4$ alkoxide, β-diketonate, cyclic amido, cyclic tris-alkoxoamine, and $C_6$–$C_{10}$ aryl; and each of $R^1$ and $R^2$ is independently selected from $C_1$–$C_8$ alkyl, $C_1$–$C_8$ alkoxy, $C_6$–$C_8$ cycloalkyl, $C_6$–$C_{10}$ aryl, $C_1$–$C_4$ carboxyl, and —$SiR^3_3$ wherein each $R^3$ is independently selected from H and $C_1$–$C_4$ alkyl. Bismuth-containing films of the invention may be utilized in the construction of spatial light modulator devices, as buffer layers for the fabrication of ferroelectric material devices, and in dielectric, ferroelectric and superconductor thin film applications.

28 Claims, 4 Drawing Sheets

METHOD OF FORMING BISMUTH-CONTAINING FILMS BY USING BISMUTH AMIDE COMPOUNDS

BACKGROUND OF THE INVENTION

1. Field of the Invention

The present invention relates to bismuth precursor source compounds and compositions, and to a process for vapor phase deposition of bismuth-containing films on substrates utilizing such compounds and compositions.

2. Description of the Related Art

Bismuth-containing materials are useful for a number of applications, including, but not limited to, dielectric/ferroelectric $SrBi_2Ta_2O_9$ (SBT), high temperature superconducting bismuth strontium calcium copper oxide (BSCCO) materials, and dielectric bismuth oxide films. Incorporation of bismuth into thin films for these and other applications has been problematic using conventional CVD precursors such as $Bi(OEt)_3$, $BiPh_3$, $Bi(thd)_3$, etc. due to low volatility or limited thermal stability.

Accordingly, there is a need in the art for precursor compositions for deposition of bismuth to form bismuth-containing films and material layers.

Concerning known bismuth organometallic compounds, Clegg, et al., *Inorg. Chem.* 1991, 30, 4680–4682, discloses bismuth amides including $Bi(NMe_2)_3$ and $Bi(NPh_2)_3$ as bismuth amide compositions whose structure has been characterized by the authors. This article also states that apart from its potential usefulness as a precursor to bismuth chemistry in general, the dimethylamide bismuth compound disclosed in the article is extremely volatile and thus potentially valuable for chemical vapor deposition work. Other amides which have been reported include: $Bi(NR_2)_3$ wherein R=Me, Et, n—Pr; $Bi(N(SiMe_3)_2)_3$; $Bi(N(Me)SiMe_3)_3$; $Bi(Me)_2(N(Me)SiMe_3)$; $BiCl_2(NEt_2)$; $BiBr_2(NMe_2)$; $BiI(NHR)_2$ wherein R=n—Pr, n—Bu; and $BiMe_x(N(Me)SiMe_3)_y$, wherein x=1, y=2 or x=2, y=1.

Among the various bismuth-containing films, bismuth-silicon-oxide films are potentially usefully employed for a variety of microelectronic and optoelectronic applications. Such bismuth-silicon compositions include sillenite, $Bi_{12}SiO_{20}$, or BSO, a photorefractive material that is capable of high spatial resolution along with high speed switching and low switching energies.

BSO films find potential application as spatial light modulators (SLMs). SLMs are devices capable of modifying the amplitude, frequency, phase or polarization of an optical field. One or more of these properties is modulated when an intrinsic property of the SLM (e.g., refractive index, dielectric constant, absorbance, etc.) is altered by an externally applied electrical or optical signal. The ability of SLMs to modulate a two-dimensional optical wavefront can result in enormous signal processing enhancement and flexibility as compared with one-dimensional electronic modulation (see, for example, Neff, J. A., et al., "Two-Dimensional Spatial Light Modulators: A Tutorial," Proc. IEEE, 1990, 78, 826).

The central and varied roles of SLMs makes them pivotal for the development of future optical processing systems, and the use of SLMs in applications such as neural networks, sensors, flat panel displays, high speed interconnections and memory technologies. In fact, applications of one- and two-dimensional SLMs could encompass nearly every optical signal processing/computer architecture conceived.

Most commercial SLMs are based on liquid-crystal technology; while inexpensive, these devices have low contrast ratios, are relatively slow, and are subject to light scatter and non-uniformity.

In the fabrication of SLM devices using BSO, as well as other applications involving bismuth-containing thin films, the art continues to seek additional bismuth precursor compounds and compositions useful in the formation of such films.

Accordingly, it is an object of the present invention to provide improved compositions and methods for forming Bi-containing films on substrates.

It is another object of the present invention to provide improved bismuth precursors and method for making bismuth-containing SLM structures and devices.

It is a further object of the invention to provide precursors and method for forming bismuth oxide films on substrates.

It is yet another object of the invention to provide precursors and method for forming sillenite films on substrates.

Other objects and advantages of the present invention will be more fully apparent from the ensuing disclosure and appended claims.

SUMMARY OF THE INVENTION

The present invention relates to the formation of bismuth-containing layers on substrates, including, compositions and methods for such purpose, and to structures, e.g., microelectronic devices and device precursor structures, including bismuth-containing layers therein.

In one aspect, the invention relates to a process of forming a bismuth-containing material layer on a substrate, comprising bubbler delivery or liquid delivery vaporization of a bismuth amide source reagent to form a bismuth-containing source vapor, and deposition on the substrate of bismuth from the bismuth-containing source vapor, to form the bismuth-containing material layer on the substrate.

The bubbler delivery of the bismuth amide source reagent includes the contacting of a carrier gas with the bismuth amide source reagent in a bubbler zone to generate a bismuth-containing source vapor which is incorporated in the carrier gas stream and conveyed to the vapor deposition zone.

The liquid delivery vaporization of the bismuth amide source reagent involves the solubilization or suspension of the bismuth amide source reagent in a suitable solvent medium, as a bismuth amide precursor composition which is delivered to a vaporization zone for vaporization of the bismuth amide from the precursor composition. The resulting vapor then is conveyed to the vapor deposition zone, in which bismuth is deposited on the substrate in the deposition zone.

The invention additionally contemplates precursor compositions of bismuth amide compounds for liquid delivery vaporization of the bismuth amide component for subsequent deposition on the substrate in the deposition zone. Such precursor compositions may comprise bismuth amide compounds in suitable solvent media including solvents such as tetrahydrofuran, butyl acetate, toluene, ethers (e.g., diphenyl ether, diethyl ether, etc.) and $C_1$–$C_{10}$ alkane solvents.

The invention also contemplates novel bismuth amide compounds of the formula $Bi(NR^1R^2)_3$. Examples of such compounds include tris(dicyclohexylamido)bismuth, tris(diphenylamido)bismuth, tris(cyclohexylamido)bismuth, and tris(phenylamido)bismuth.

Mixed-ligand systems such as $Bi(NR_2)_2R'$ or $Bi(NR_2)R'_2$ that contain fewer than three amido groups in conjunction with other organic ligands, such as β-diketonate, cyclic (mono- or poly-) amido, cyclic tris-alkoxoamines, alkyl or aryl, are also contemplated as precursor compositions for vapor deposition on substrates of bismuth-containing layers in the practice of the invention.

The invention in another aspect relates to the formation on a substrate of a layer of sillenite, i.e., bismuth-silicon-oxide $Bi_{12}SiO_{20}$ (BSO), as a photorefractive material capable of high spatial resolution along with high speed switching and low switching energies. The deposition of large area photorefractive thin films is contemplated, which allows simplification of optical/image processing systems and increase the circuit density and speed for massively parallel computers.

Yet another aspect of the invention relates to the formation of a BSO material, e.g., as a thin film material layer on a substrate, by vapor deposition using a single source Bi—Si precursor compound, having bismuth as well as silicon atoms therein. The single source precursor compound may be of varying type, and may for example comprise a coordination compound including a ligand such as a tetrahydrofuranyl group. For example, bismuth trimethylamides may be employed as the single source precursor, as well as other compounds such as tris(triphenylsiloxy)bismuth and other bismuth siloxides, and their adducts.

Alternatively, the invention contemplates the formation on a substrate of a BSO material layer, by vapor deposition using a dual source precursor chemistry, in which separate bismuth and silicon source compounds are employed (i.e., the bismuth source compound and the silicon source compound are separate and distinct from one another). For example, the silicon source compound may comprise a silane, silane derivative, such as t-butylsilane, di-t-butylsilane, silane substituted with alkoxy and/or carboxy groups, or other silicon source composition. The bismuth source compound may comprise a compound such as the bismuth amide compounds described hereinabove, or the bismuth source compound may comprise a precursor such as triphenylbismuth, tris(b-diketonate)bismuth, or bismuth alkoxides such as tris(ethyldimethylmethoxy)bismuth, or bismuth carboxylates such as tris(pivalate)bismuth.

In one aspect of the method of forming a BSO layer on a substrate, silane is employed as a source reagent for the silicon to be incorporated in the BSO layer, and the silane is generated in situ in the process, by thermolytic reaction of butylsilane species, such as $SiH_3(t—Bu)$ and $SiH_2(t—Bu)_2$, to yield silane.

In another aspect of the method of forming a BSO layer on a substrate, silicon dioxide is formed on the substrate concurrently with deposition of the bismuth component on the substrate, by oxidation of a silicon amide of the formula $Si(NR_2)_4$ wherein R is lower alkyl, e.g., methyl or ethyl, and oxidation is carried out in the presence of oxygen or ozone as the oxidizing medium. The introduction and mixing, of oxidants is employed to limit particle formation.

A still further aspect of the invention relates to structures incorporating a BSO layer formed on a substrate by MOCVD in accordance with the invention. Such structure may comprise a spatial light modulator device, e.g., wherein the BSO film is formed on a substrate such as sapphire or other base material, or a structure in which the BSO film is employed as a buffer layer on the substrate, for an overlying ferroelectric layer, such as a thin film of $Bi_4Ti_3O_{12}$.

Other aspects, features and embodiments of the invention will be more fully apparent from the ensuring disclosure and the appended claims.

DETAILED DESCRIPTION OF THE INVENTION, AND PREFERRED EMBODIMENTS THEREOF

The present invention involves the vapor deposition formation of bismuth-containing layers on substrates, using precursors which permit bismuth-containing layers of good morphological and functional characteristics to be achieved, without the problems which have attended the use of bismuth precursors of the prior art having low volatility or limited thermal stability.

The precursors of the invention comprise bismuth amide reagents. As mentioned earlier herein, the prior art has used bismuth precursors such as $Bi(OEt)_3$, $BiPh_3$ and $Bi(thd)_3$ with limited or unsatisfactory results. The process of the present invention represents an improvement over such prior art bismuth deposition practice, by the use of bismuth amide reagents having good volatility and thermal stability characteristics for vapor phase deposition, by bubbler delivery or by liquid delivery vaporization techniques.

The process of the present invention thus contemplates forming a bismuth-containing material layer on a substrate, involving bubbler delivery or liquid delivery vaporization of a bismuth amide source reagent to form a bismuth-containing, source vapor. Bismuth then is deposited on the substrate from the bismuth-containing source vapor, to yield the bismuth-containing material layer on the substrate.

Figure 1:
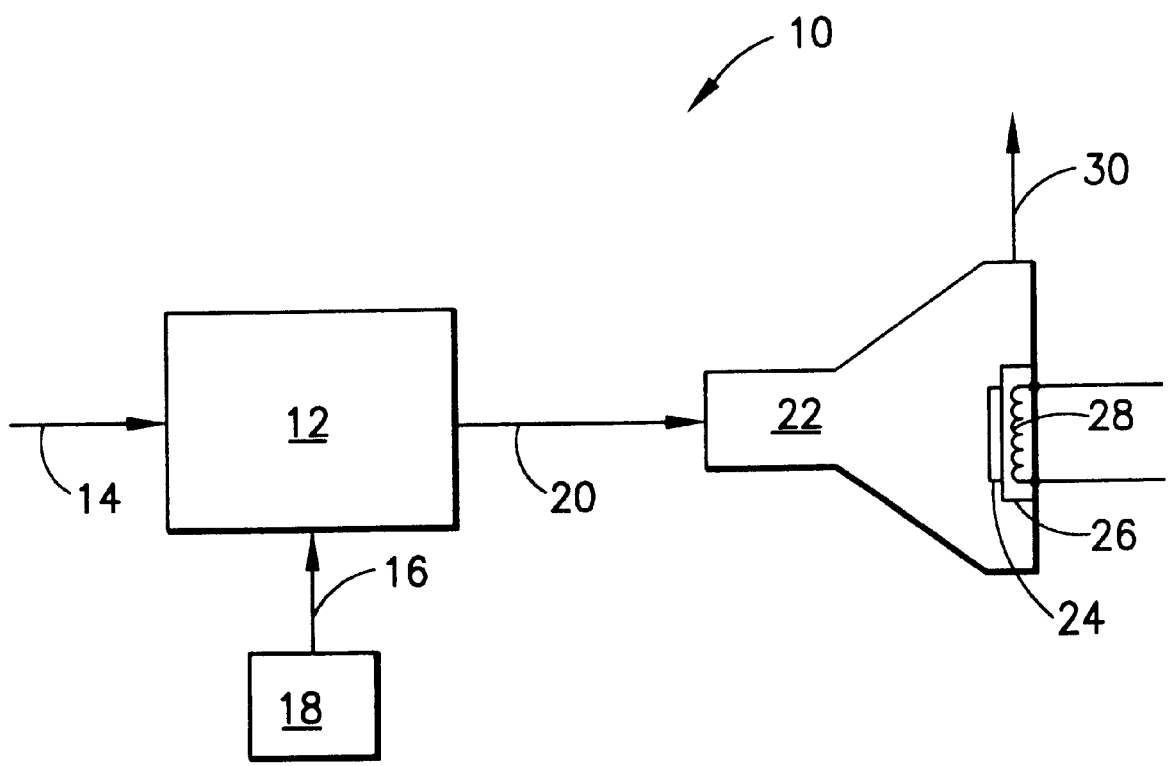
FIG. 1 is a schematic representation of a process system for the formation of a bismuth-containing film on a substrate.

FIG. 1 is a schematic representation of a process system 10 for the formation of a bismuth-containing film on a substrate. The process system includes a supply unit 12 for bismuth-containing source reagent vapor. Such supply unit may comprise a liquid delivery and vaporizer assembly, of suitable type, such as that shown in U.S. Pat. No. 5,204,314 to Peter S. Kirlin, et al. and U.S. Pat. No. 5,536,323 to Peter S. Kirlin, et al., the disclosures of which hereby are incorporated herein in their entirety. The supply unit 12 receives a suitable bismuth precursor composition in line 16 from precursor supply reservoir 18. The liquid precursor may comprise a neat bismuth amide compound or one dissolved in a suitable solvent such as toluene, hexane, octane, tetrahydrofuran (thf) or the corresponding tetrahydropyran solvent (thp), or the like.

The source reagent solution is flowed to a vaporizer element or zone in the supply unit 12 for vaporization, and flow of the resulting volatilized bismuth composition in a suitable carrier gas. The carrier gas is introduced in feed conduit 14 to the supply unit 12, and may be flowed over the vaporizer element to entrain the volatilized bismuth composition therein. Illustrative carrier gas species include argon, nitrogen, helium, etc., and the choice of a specific co-reactant gas species depending on the nature of the film desired to be desired on the specific substrate employed. For example, oxygen and/or nitrous oxide may be used for oxide films.

The bismuth-containing precursor vapor from the vaporization operation is discharged from the supply unit 12 in line 20 and flowed to the chemical vapor deposition chamber 22. A substrate 24 is mounted on a susceptor 26 heated by electrical resistance heating element 28.

The bismuth-containing precursor vapor is flowed into the chemical vapor deposition chamber 22 and contacted with the substrate element 24 in the presence of a reactant gas (i.e., oxygen), resulting in deposition of bismuth-containing film on the substrate from the vapor phase. The contacted vapor then is discharged from the chemical vapor deposition chamber 22 in line 30, and may be recycled, processed for effluent treatment thereof, or otherwise be disposed of or further processed.

The supply unit 12 may instead of a liquid delivery vaporization system comprise a conventional bubbler apparatus in which the bismuth amide source reagent is disposed and subjected to bubbling processing to generate a bismuth-containing vapor, which then is flowed from the supply unit 12 to the chemical vapor deposition chamber 22 as previously described.

Although the art has deposited bismuth from other precursor bismuth-containing compounds, bismuth amide precursor compounds have not been used for such purpose, and the bubbler and liquid delivery vaporization MOCVD usage of bismuth amides for such purpose represents a substantial advance over prior practice.

The bismuth amide compounds which are employed for liquid delivery vaporization of the bismuth amide component for subsequent deposition on the substrate in the deposition zone comprise bismuth amide compounds in suitable solvent media including organic solvents such as tetrahydrofuran, toluene, hexane, octane etc.

The process of the present invention may employ bismuth amide compounds of the formula $$BiL^1_xL^2_y(NR^1R^2)_z$$

wherein,
x, y and z are integers of from 1 to 3;
x+y+z=3;
each of $L^1$ and $L^2$ is independently selected from $C_1$–$C_4$ alkyl, β-diketonate, cyclic amido, cyclic tris-alkoxoamine, and $C_6$–$C_{10}$ aryl; and
each of $R^1$ and $R^2$ is independently selected from $C_1$–$C_8$ alkyl, $C_1$–$C_8$ alkoxy, $C_6$–$C_8$ cycloalkyl, $C_6$–$C_{10}$ aryl, $C_1$–$C_4$ carboxyl, and —$SiR^3_3$ wherein each $R^3$ is independently selected from H and $C_1$–$C_4$ alkyl.

Illustrative examples of such compounds include, but are not limited to:
tris(dimethylamido)bismuth;
tris(diethylamido)bismuth;
tris(diphenylamido)bismuth;
tris(di-n-propylamido)bismuth;
tris(di(trimethylsilyl)amido)bismuth;
tris(dicyclohexylamido)bismuth;
tris(cyclohexylamido) bismuth;
tris(phenylamido) bismuth;
((trimethylsilyl)methylamido)dimethylbismuth;
(diethylamido)dichlorobismuth;
(dimethylamido)dibromobismuth;
tris(N-ethyl,N',N'-dimethyl-1,3-propanediamido) bismuth; and
bis(dipropylamido)iodobismuth,
although any suitable bismuth amide compounds may be employed in the broad practice of the invention.

Thus, mixed-ligand systems such as $Bi(NR_2)_2R'$ or $Bi(NR_2)R'_2$ that contain fewer than three amido groups in conjunction with other organic ligands, such as β-diketonate, alkyl or aryl, cyclic (mono- or poly-) amido, cyclic tris-alkoxoamines, etc., are contemplated as useful precursor compositions for vapor deposition on substrates of bismuth-containing layers in the practice of the invention.

The process conditions usefully employed for chemical vapor deposition of bismuth from the vaporized precursor may readily be determined without undue experimentation, to ascertain the appropriate temperature, pressure and flow rate conditions which are advantageously employed to form superior structural and functional bismuth-containing films in the practice of the invention.

Bismuth tris(amides) are readily prepared by metathesis reactions such as:

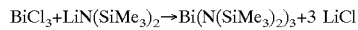

or with an ether adduct of lithium bis(trimethylsilylamide):

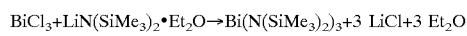

The mixed ligand systems may be prepared in a similar fashion.

The bismuth amide precursor compositions may be employed to form bismuth oxide films, as well as other bismuth-containing layers on the substrate on which bismuth is deposited from the precursor vapor. Such bismuth amide precursors have particular advantages in such application over prior art bismuth-containing precursor compounds.

Figure 2:
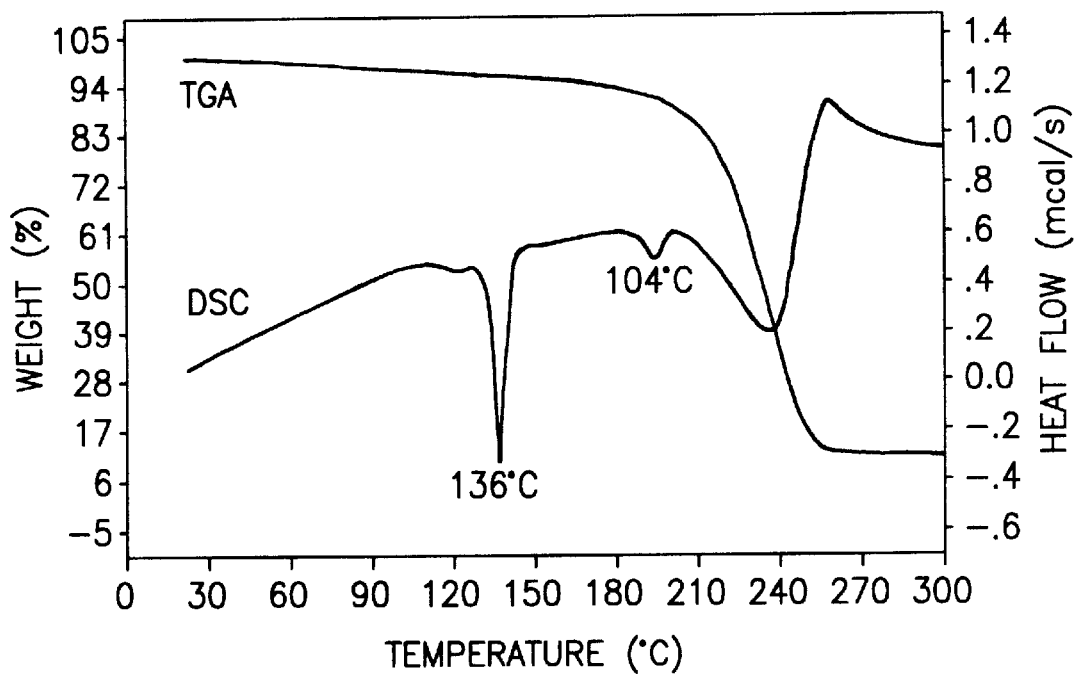
FIG. 2 depicts the thermal gravimetric analysis (TGA) and differential scanning calorimetry (DSC) of $Bi(N(SiMe_3)_2)_3$ in argon gas.

As an example, thermal analysis of $Bi(N(SiMe_3)_2)_3$ confirms that much lower temperatures are required for the amide to form bismuth oxide as compared to $BiPh_3$. In argon, sublimation of $Bi(N(SiMe_3)_2)_3$ occurs from 220° C. to 270° C. at atmospheric pressure, as shown by the thermogravimetric analysis (TGA) and differential scanning calorimetry (DSC) curves in the graph of FIGS. 2 and 3. These data were generated at a heating rate of 10° C./minute.

Figure 3:
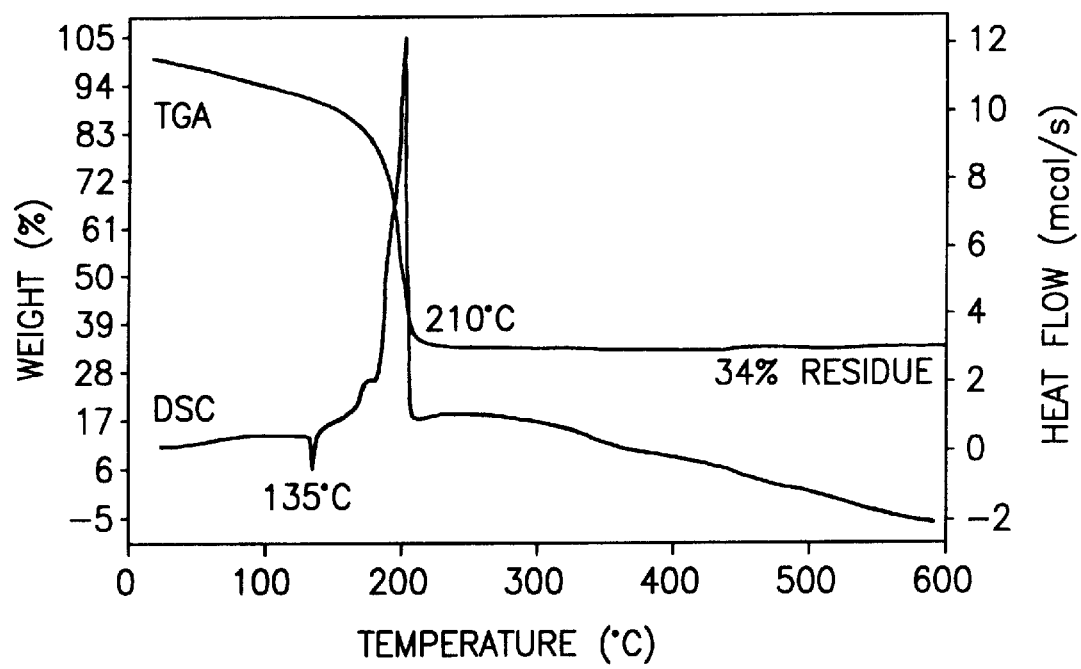
FIG. 3 depicts the thermal gravimetric analysis (TGA) and differential scanning calorimetry (DSC) of $Bi(N(SiMe_3)_2)_3$ in oxygen gas.

In oxygen, as a further example, decomposition of $Bi(N(SiMe_3)_2)_3$ begins at 150° C. and is completed by 220° C. as shown in the graph of FIG. 3, by the corresponding TGA and DSC curves.

Figure 4:
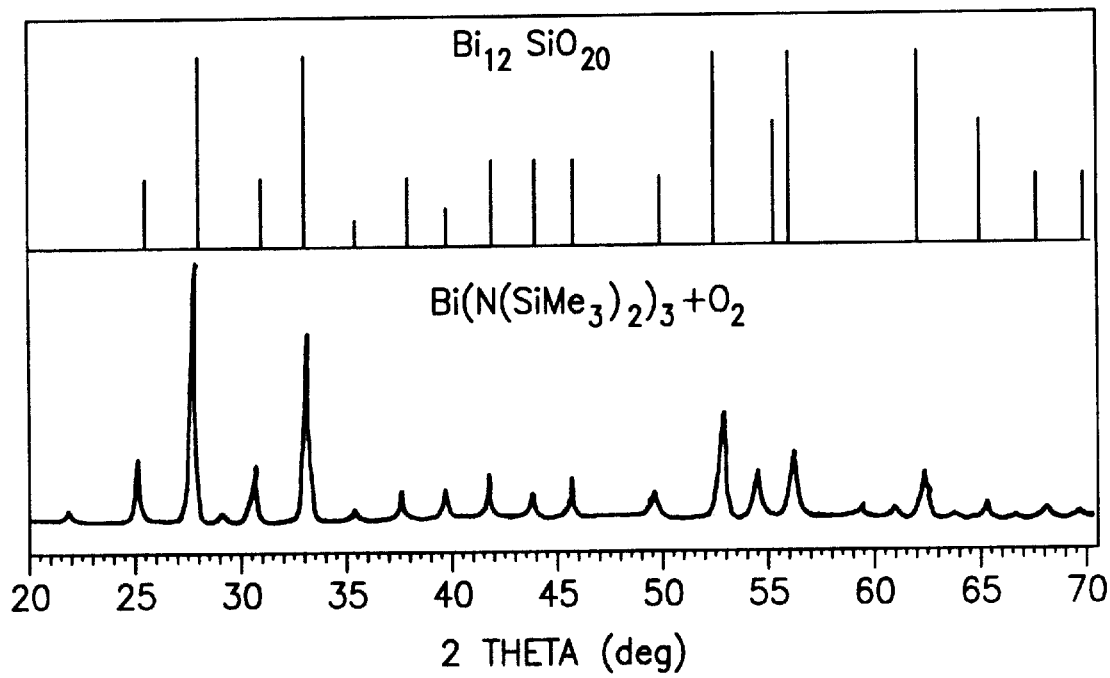
FIG. 4 is a powder x-ray diffraction spectrum of the oxidation product of $Bi(N(SiMe_3)_2)_3$, the residue produced by the decomposition of $Bi(N(SiMe_3)_2)_3$ in atmospheric oxygen gas with heating to 600° C., and a reference sample of BSO ($Bi_{12}SiO_{20}$).

The product of the thermal oxidation of $Bi(N(SiMe_3)_2)_3$ can be examined by powder X-ray diffraction (XRD), yielding the XRD spectrum shown in FIG. 4.

Figure 5:
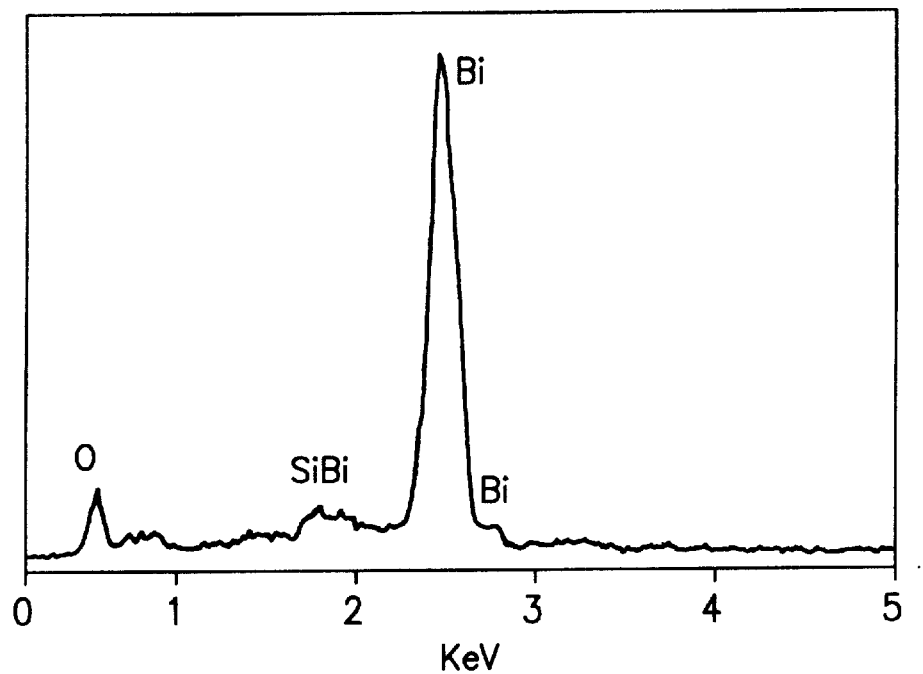
FIG. 5 is an energy dispersive spectroscopy (EDS) plot of $Bi(N(SiMe_3)_2)_3$ oxidation residue.

FIG. 5 is an energy dispersive spectroscopy (EDS) plot of the $Bi(N(SiMe_3)_2)_3$ oxidation residue. This analysis shows the product to be a bismuth-containing oxide, closely resembling sillenite, $Bi_{12}SiO_{20}$, as depicted in the top portion of FIG. 4.

The triphenylbismuth compound sublimes in a similar range to the amide compound ($Bi(N(SiMe_3)_2)_3$), and begins thermal decomposition in oxygen at about 200° C. but does not form bismuth oxide until 480° C., approximately 280° C. higher than the temperature that is required for Bi(N(Si- Me$_3$)$_2$)$_3$ to form the bismuth oxide product. At 100 mtorr pressure, Bi(N(SiMe$_3$)$_2$)$_3$ sublimes at 110° C. and is readily soluble in a variety of organic solvents, rendering, it highly suitable for both bubbler and liquid delivery to a CVD reactor.

The reduction in decomposition temperature in oxygen of the bismuth amide compounds is a significant advantage over use of other bismuth compounds utilized in the prior art.

In the formation of BSO films on substrates using bismuth amide precursor compositions of the invention, e.g., tris (trimethylsilylamido)bismuth, it is found that the deposition of the film of BSO may be conducted at very low temperatures, e.g., as low as 300° C. or even less. This is a substantial improvement over the temperatures of 600–700° C. which are characteristic of BSO film formation using the precursor compounds of the prior art.

The conversion of bismuth amides to the solid state oxide is substantially independent of the nature of the amide ligand functionalities. The amide groups of the bismuth amide compound can be modified to impart the desired volatility, stability and ease of synthesis desired for a given application of the bismuth amide precursor. The phase and purity of the deposited material will depend upon the specific precursor used in addition to the rate of film growth, the substrate employed, and the deposition conditions utilized.

Accordingly, the bismuth amide precursors of the invention may be employed to form a layer of sillenite, i.e., BiSiO$_{20}$(BSO), on a substrate as a photorefractive material capable of high spatial resolution along with high speed switching and low switching energies. The BSO film may be formed on any suitable substrate, and may be formed as a large area photorefractive thin film for spatial light modulator device fabrication.

Such BSO material layer may be formed on the substrate by vapor deposition using a single source Bi—Si precursor compound, having bismuth as well as silicon atoms therein. The single source precursor compound may be any of the previously mentioned illustrative compounds. The single source precursor compound may for example be a coordination compound including a ligand such as a tetrahydrofuranyl group.

Alternatively, a BSO material layer may be formed on the substrate by vapor deposition using a dual source precursor chemistry, in which separate bismuth and silicon source compounds are employed. The silicon source compound may comprise a silane, silane derivative, such as t-butylsilane, di-t-butylsilane, silane substituted with alkoxy and/or carboxy groups, or other silicon source composition. The bismuth source compound may comprise a compound such as the bismuth amide compounds described hereinabove, or the bismuth source compound may comprise a precursor such as triphenylbismuth, tris(b-diketonato)bismuth compounds such as Bi(thd)$_3$, bismuth alkoxides such as tris(ethyldimethylmethoxy)bismuth, or carboxylbismuth compounds such as tris(t-butylcarboxy) bismuth.

In forming a BSO layer on a substrate, silane may be employed as a source reagent for the silicon to be incorporated in the BSO layer. As an alternative to providing silane in the first instance, silane may be generated in situ in the process system, by thermolytic reaction of SiH$_3$(t—Bu) and Si—H$_2$(t—Bu)$_2$ to yield silane.

Figure 6:
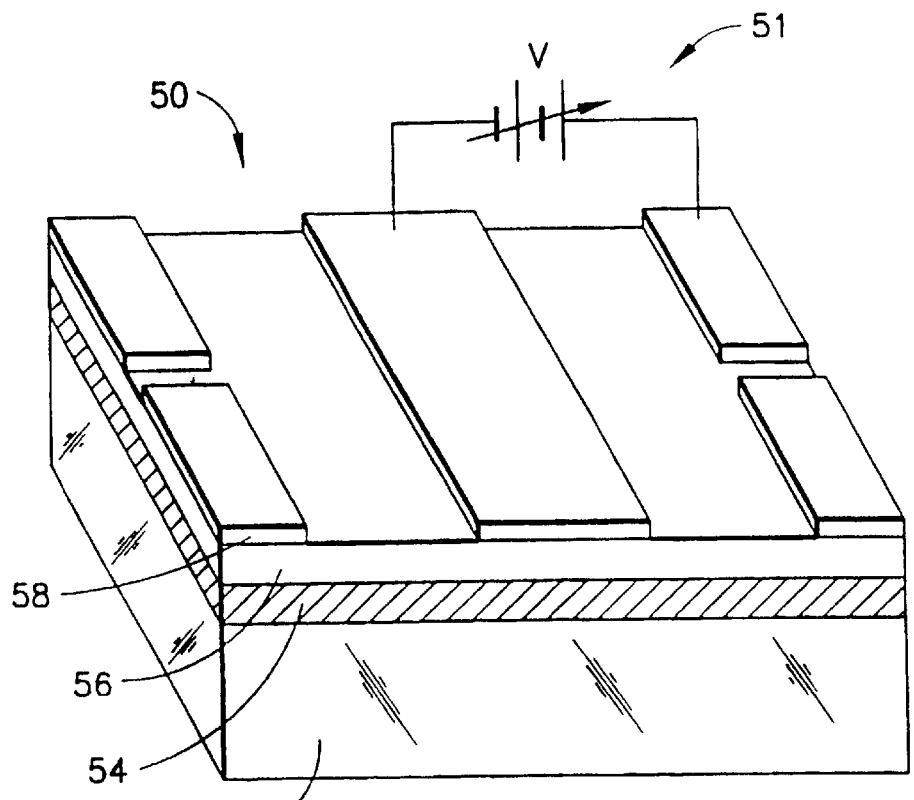
FIG. 6 is a perspective view of an integrated BSO thin film spatial light modulator device, comprising a BSO film formed in accordance with the present invention.

As another alternative for forming a BSO layer on a substrate, silicon dioxide may be formed on the substrate concurrently with deposition of the bismuth component, by oxidation of a silicon amide of the formula Si(NR$_2$)$_4$ wherein R is lower alkyl, e.g., methyl ethyl, propyl, butyl, etc., and oxidation is carried out in the presence of oxygen or ozone as the oxidizing medium FIG. 6 shows a perspective schematic view of a thin film spatial light modulator device 50 for transmission measurement. The device comprises a substrate 52 which may for example comprise sapphire or other suitable substrate material of constriction. On the substrate is deposited a BSO layer 54, which may for example have a thickness on the order of 1 micrometer. Deposited on the BSO layer is an aluminum-tantalum-oxide (ATO) insulator layer 56, which may likewise have a thickness on the order of 1 micrometer. Deposited on the insulator layer 56 is a pattern of aluminum electrodes 58, which may be formed with a thickness on the order of 2000 Angstroms.

The switching of Bi$_{12}$SiO$_{20}$ in such device is effected by application of an optical control signal which causes a charge separation. The resultant refractive index (birefringence) change alters the polarization of the light being transmitted.

A BSO thin film layer formed in accordance with the invention may be employed using a photorefractive material for both detection and modulation, e.g., in a readout optical modulator (ROM) device. The ROM device may be operated by illuminating with a spatially varying blue light, so that free charge carriers are generated, with the application of an external voltage 51 causing, a corresponding variation in the refractive index of the BSO. Since red light does not generate additional free charge carriers it can be used to measure the refractive index variations. Such ROM device may be used in fabricating integrated optical devices for color conversion or incoherent-to-coherent image conversion. BSO thin films fabricated with the bismuth source compositions of the invention may be incorporated in various devices for phase conjugation, two wave mixing and hologram recording devices.

BSO films formed in accordance with the present invention may also be employed in applications such as optical waveguides, and devices that utilize the photo- and electrochromic behavior observed for transition metal-doped BSO.

Figure 7:
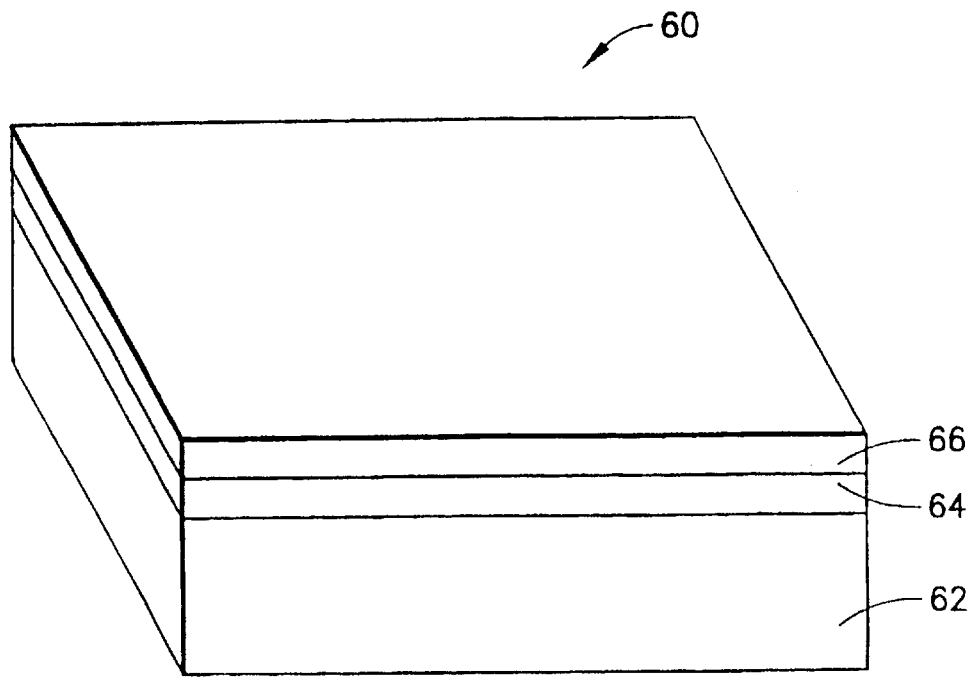
FIG. 7 is a perspective view of a structure including a BSO film on a substrate, overlaid by a ferroelectric material layer deposited on the BSO film.

As another example of application of BSO films formed in accordance with the present invention, FIG. 7 shows a perspective schematic view of a ferroelectric material device 60 comprising a substrate 62 which may for example comprise sapphire or other suitable substrate material of construction. On the substrate is deposited a BSO buffer layer 64, and overlying the buffer layer is a ferroelectric layer 66, such as a thin film of Bi$_4$Ti$_3$O$_2$.

In contrast to the BSO film formation method of the present invention, bulk single crystal BSO grown by the Czochralski method exhibits poor compositional uniformity and difficulties in polishing the crystal layer to less than 200 mm in thickness results in degraded resolution. Increased resolution may be attained by formation of thin film spatial light modulators (TF-SLMs), e.g., by electron cyclotron resonance (ECR) plasma sputtering of a bismuth/silicon target in oxygen at 600° C. to yield crystalline, epitaxial BSO thin films, but the deposition of BSO thin films by CVD has received very limited attention in the art.

The reasons for this inattention include the limitations of the process when using bismuth precursor compounds of the prior art. For example, in deposition using bismuth metal and Si(OMe)$_4$, low growth rates are experienced due to the limited volatility of the bismuth. As another example, growth using precursors such as BiMe$_3$ and Si(OR)$_4$ (R=Me, Et) at 700° C. resulted in higher growth rates, but required narrow process conditions to limit gas phase nucleation due to reaction of the bismuth precursor with oxygen.

As an alternative to the use of single source precursors, dual source reagent systems may be employed, e.g., a solution containing separate bismuth organometallic source compound(s) and silicon organometallic source compound (s).

The single source precursor compound may be of varying type, and may for example comprise a coordination compound including a ligand such as a tetrahydrofuranyl group. Illustrative single source precursor compounds include silicon-containing bismuth amides, e.g., $Bi(N(SiMe_3)_2)_3$, bismuth siloxide compounds, e.g., tris(triphenylsiloxy) bismuth, and adducts thereof. The siloxide $Bi(OSiPh_3)_3$ is readily formed by alcoholysis of $Bi(NMe_2)_3$ using $HOSiPh_3$:

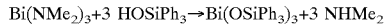
$Bi(NMe_2)_3 + 3\ HOSiPh_3 \rightarrow Bi(OSiPh_3)_3 + 3\ NHMe_2$ $Bi(OSiPh_3)_3$ is soluble in coordinating solvents such as tetrahydrofuran (thf) which could be used for liquid delivery processing. Correspondingly, the adduct $Bi(OSiPh_3)_3(thf)$ may be formed (or other adduct species using ligands such as glymes (e.g., tetraglyme), polyamines, etc.) and utilized in other solvent media, for liquid delivery purposes. It will be appreciated that numerous species of single source precursor compounds are possible and are contemplated within the broad scope of the present invention.

Analogously, numerous species of dual source precursors for bismuth and silicon are possible and contemplated in the broad practice of the invention. As mentioned, silane may be employed as the silicon source compound, and silane and silane derivatives may be formed in situ in the process system, by thermolysis reaction of butylsilane species, such as t-butylsilane and di-t-butylsilane, to yield silane via isobutene elimination. These butylsilane reactants are air stable and volatile liquids with boiling points of 29° C. and 128° C., respectively.

Additionally, MOCVD of silicon dioxide can be carried out by low temperature oxidation of silicon amides such as $Si(NR_2)_4$ wherein R=methyl or ethyl, using oxygen or ozone as the oxidant medium.

For separate source reagents for formation of BSO films, Table I below sets out illustrative bismuth and silicon precursors.

TABLE I

| Bismuth Precursor Compound | Silicon Precursor Compound |
|---|---|
| $BiPh_3$ | $Si(OEt)_4$ |
| $Bi(OCMe_2Et)_3$ | $Si(O-t-Bu)_2(O_2CMe)_2$ |
| $Bi(O_2C-t-BU)_3$ | $Si(O-t-Bu)_2(O_2C-t-Bu)_2$ |
| $Bi(thd)_3$ | $SiH_2(t-Bu)_2$ or $SiH_3(t-Bu)$ |
| $Bi(NMe_2)_3$ | $Si(NMe_2)_4$ |

Multicomponent precursor systems may also be employed for certain applications using transition metal doped sillenites as well as for forming the related germanium and titanium substituted materials $Bi_{12}MO_{20}$() (M=Ge, Ti).

The bismuth precursors disclosed herein can be used to form bismuth-containing oxides, ferroelectrics, superconductors, and a wide variety of microelectronic and optical thin films. Further, both conventional and liquid delivery techniques may be employed to introduce these precursors into CVD reactors.

The features and advantages of the invention are more fully shown with reference to the following examples, wherein all parts and percentages are by weight, unless otherwise expressly stated.

EXAMPLE I

One gram (0.00293 mmol) of tris(N,N-dimethyl-N'-ethylenediamine)bismuth was dissolved in 10 milliliters of diethyl ether. To this solution 1.022 (grams (3 eq., 0.0088 mmol) of N,N-dimethyl-N'-ethylenediamine was added dropwise. Upon addition of the amine the color of the solution changed from light yellow to orange. The solution was stirred for an additional 15 minutes after which the diethyl ether was removed in vacuo. The bismuth amide was isolated as an orange oil. The compound may be used in bubblers at temperatures less than 162° C.

EXAMPLE II 0.317 grams (0.00093 mmol) of $Bi(N(Me)_2)_3$ was dissolved in 10 milliliters of pentane. To this solution 0.5 gram (0.0028 mmol) of 2-(N-ethyl-m-toluidino)ethanol was added, dropwise. This solution was allowed to stand overnight and then filtered and concentrated to yield a viscous yellow oil. The product was bismuth(2-(N-ethyl-m-toluidino)ethanoxide). NMR, $(C_6D_6)$: 7.20 (t), 6.80 (s), 6.69 (t), 5.11 (s), 3.33 (m), 2.28 (s), 0.936 (m, 3H).

While the invention has been disclosed herein in terms of vapor phase deposition methods such as bubbler delivery, or liquid delivery and vaporization, for forming the bismuth-containing films and materials of the invention, it will be recognized that bismuth amide compounds as described herein may be employed in other film formation processes such as sol gel processes and MOD processes to form bismuth-containing films and materials for applications such as those disclosed illustratively herein.

While the invention has been described with reference to various illustrative aspects, features, and embodiments, it will be appreciated that other variations, modifications and other embodiments are contemplated as being within the purview of the invention, and therefore the invention as claimed is intended to be broadly construed, as including all such variations, modifications and other embodiments within its spirit and scope:

What is claimed is:

1. A method of forming a bismuth-containing material layer on a substrate, comprising liquid delivery vaporization of a bismuth amide source reagent to form a bismuth-containing source vapor, and deposition on the substrate of bismuth from the bismuth-containing source vapor, to form the bismuth-containing material layer on the substrate.

2. A method according to claim 1, wherein the bismuth amide source reagent comprises a bismuth amide adduct.

3. A method according to claim 1, wherein the bismuth amide source reagent comprises a bismuth amide compound in a solvent.

4. A method according to claim 1, wherein the solvent is selected from the group consisting of tetrahydrofuran, tetrahyropyran, toluene, hexane, octane, diphenyl ether, and diethyl ether.

5. A method according to claim 1, wherein the bismuth amide source reagent comprises a bismuth-containing source and a silicon-containing source, and the bismuth-containing material layer on the substrate comprises a bismuth silicon oxide material layer.

6. A method according to claim 5, wherein the bismuth-containing source compound and silicon-containing source compound are different compounds.

7. A method according to claim 6, wherein the different compounds comprise a bismuth-containing source compound and a silicon-containing source compound independently selected from the group consisting of:

| Bismuth-Containing Source Compound | Silicon-Containing Source Compound |
|---|---|
| $BiPh_3$ | $Si(OEt)_4$ |
| $Bi(OCMe_2Et)_3$ | $Si(O\text{-}t\text{-}Bu)_2(O_2CMe)_2$ |
| $Bi(O_2C\text{-}t\text{-}Bu)_3$ | $Si(O\text{-}t\text{-}Bu)_2(O_2C\text{-}t\text{-}Bu)_2$ |
| $Bi(thd)_3$ | $SiH_2(t\text{-}Bu)_2$ or $SiH_3(t\text{-}Bu)$ |
| $Bi(NMe_2)_3$ | $Si(NMe_2)_4$. |

8. A method according to claim 6, wherein the different compounds comprise a silane as the silicon source compound.

9. A method according to claim 8, wherein the silane is formed by thermolysis reaction of a butylsilane compound.

10. A method according to claim 9, wherein the butylsilane compound is selected from the group consisting of t-butylsilane and di-t-butylsilane.

11. A method according to claim 6, wherein the silicon-containing source compound is selected from the group consisting of silanes and substituted silanes.

12. A method according to claim 11, wherein the silicon-containing source compound comprises a substituted silane whose substituents are selected from alkoxy and carboxy groups.

13. A method according to claim 6, wherein the bismuth-containing source compound is selected from the group consisting of bismuth amide compounds, arylbismuth compounds, tris(b-diketonate)bismuth compounds, bismuth alkoxide compounds, and bismuth carboxylate compounds.

14. A method according to claim 1, wherein the bismuth amide source reagent includes an ethylene bridged polyamine moiety.

15. A method of forming a bismuth-containing material layer on a substrate, comprising liquid delivery vaporization of a bismuth amide source reagent to form a bismuth-containing source vapor, and deposition on the substrate of bismuth from the source vapor to form the bismuth-containing layer on the substrate, wherein the bismuth amide source reagent is a bismuth amide compound of the formula:

$$BiL^1{}_xL^2{}_y(NR^1R^2)_z$$

wherein:
z is an integer of from 1 to 3;
x+y+z=3;
each of $L^1$ and $L^2$ is independently selected from $C_1$–$C_4$ alkyl, halo, β-diketonate, cyclic amido, cyclic tris-alkoxoamine, and $C_6$–$C_{10}$ aryl;
each of $R^1$ and $R^2$ is independently selected from $C_1$–$C_8$ alkyl, $C_1$–$C_8$ alkoxy, $C_6$–$C_8$ cycloalkyl, $C_6$–$C_{10}$ aryl, $C_1$–$C_4$ carboxyl, and —$SiR^3{}_3$ wherein each $R^3$ is independently selected from H and $C_1$–$C_4$ alkyl.

16. A method according to claim 15, wherein each L is independently selected from the group consisting of $C_1$–$C_4$ alkyl, aryl and trimethylsilyl ligands.

17. A method of forming a bismuth-containing material layer on a substrate, comprising liquid delivery vaporization of a bismuth amide source reagent to form a bismuth-containing source vapor, and deposition on the substrate of bismuth from the bismuth-containing source vapor, to form the bismuth-containing material layer on the substrate, wherein the bismuth amide source reagent comprises a compound of the formula $Bi(NR^1R^2)_3$, wherein each of $R^1$ and $R^2$ is independently selected from $C_1$–$C_8$ alkyl, $C_1$–$C_8$ alkoxy, $C_6$–$C_8$ cycloalkyl, $C_6$–$C_{10}$ aryl, $C_1$–$C_4$ carboxyl, and —$SiR^3{}_3$ wherein each $R^3$ is independently selected from H and $C_1$–$C_4$ alkyl.

18. A method of forming a bismuth-containing, material layer on a substrate, comprising liquid delivery vaporization of a bismuth amide source reagent to form a bismuth-containing source vapor, and deposition on the substrate of bismuth from the bismuth-containing source vapor, to form the bismuth-containing material layer on the substrate, wherein the bismuth amide source reagent comprises a compound selected from the group consisting of:
tris(dimethylamido)bismuth;
tris(diethylamido)bismuth;
tris(diphenylamido)bismuth;
tris(di-n-propylamido)bismuth;
tris(di(trimethylsilyl)amido)bismuth;
tris(dicyclohexylamido)bismuth;
tris(cyclohexylamido) bismuth;
tris(phenylamido) bismuth;
((trimethylsilyl)methylamido)dimethylbismuth; and
tris(N, N-dimethyl,N'-ethylenediamine) bismuth.

19. A method of forming a bismuth-containing material layer on a substrate, comprising liquid delivery vaporization of a bismuth amide source reagent to from a bismuth-containing source vapor, and deposition on the substrate of bismuth from the bismuth-containing source vapor, to form the bismuth-containing material layer on the substrate, wherein the bismuth amide source reagent comprises a compound of the formula:

$$BiL^1{}_xL^2{}_y(NR^1R^2)_z$$

wherein:
z is 1 or 2;
x+y+z=3;
each of $L^1$ and $L^2$ is independently selected from $C_1$–$C_4$ alkyl, halo, β-diketonate, cyclic amido, cyclic tris-alkoxoamine, and $C_6$–$C_{10}$ aryl; and
each of $R^1$ and $R^2$ is independently selected from $C_1$–$C_8$ alkyl, $C_1$–$C_8$ alkoxy, $C_6$–$C_8$ cycloalkyl, $C_6$–$C_{10}$ aryl, $C_1$–$C_4$ carboxyl, and —$SiR^3{}_3$ wherein each $R^3$ is independently selected from H and $C_1$–$C_4$ alkyl.

20. A method of forming a bismuth silicon oxide material layer on a substrate, comprising liquid delivery vaporization of a bismuth amide source reagent to form a bismuth-containing source vapor, and deposition on the substrate of bismuth from the bismuth-containing source vapor, to form the bismuth silicon oxide material layer on the substrate, wherein the bismuth amide source reagent comprises a bismuth-containing source and silicon-containing source comprising a same compound, as a single source precursor for bismuth and silicon.

21. A method according to claim 20, wherein the same compound is selected from the group consisting of bismuth silylamide compounds and bismuth siloxide compounds.

22. A method according to claim 21, wherein the same compound is $Bi(N(SiMe_3)_2)_3$.

23. A method according to claim 21, wherein the same compound is $Bi(OSiPh_3)_3$.

24. A method according to claim 21, wherein the same compound is a Lewis base adduct.

25. A method according to claim 21, wherein the same compound is the adduct $Bi(OSiPh_3)_3(thf)$.

26. A method of forming a bismuth-containing material layer on a substrate, comprising liquid delivery vaporization of a bismuth amide source reagent to form a bismuth-containing source vapor, and deposition on the substrate of bismuth from the bismuth-containing source vapor, to form the bismuth-containing material layer on the substrate, wherein the bismuth amide source reagent comprises a bismuth-containing source and a silicon-containing source, and the bismuth-containing material layer on the substrate comprises a bismuth silicon oxide material layer, wherein the bismuth-containing source compound and silicon-containing source compound are different compounds, and wherein silicon dioxide is deposited on the substrate, by oxidation of a silicon amide of the formula $Si(NR_2)_4$ wherein R=methyl or ethyl, using oxygen, nitrous oxide, or ozone as an oxidant medium, concurrently with deposition on the substrate of bismuth from the bismuth-containing source vapor, to form said bismuth silicon oxide material layer on the substrate.

27. A method for forming a sillenite film on a substrate comprising depositing a bismuth- and silicon-containing film on the substrate from a vapor of a bismuth silyl amide compound of the formula $Bi(N(SiR_3)_2)_3$ wherein each R is independently selected from $C_1-C_8$ alkyl, in an oxidizing atmosphere at temperature below 300° C.

28. A method of forming a $Bi_{12}MO_{20}$ layer on a substrate, wherein M is Si, Ge, or Ti, comprising the steps of:

forming a bismuth-containing source vapor by liquid delivery vaporization of a bismuth amide source reagent;

forming an M-containing source vapor by bubbler delivery or liquid delivery of an M source reagent; and depositing bismuth on the substrate from the bismuth-containing source vapor, and M on the substrate from the M-containing source vapor, to form the $Bi_{12}MO_{20}$ layer on the substrate.

* * * * *

UNITED STATES PATENT AND TRADEMARK OFFICE
CERTIFICATE OF CORRECTION

PATENT NO : 5,902,639

DATED : May 11, 1999

INVENTOR(S) : Timothy E. Glassman; Gautam Bhandari; and Thomas H. Baum

It is certified that error appears in the above-identified patent and that said Letters Patent are hereby corrected as shown below:

| | |
|---|---|
| Abstract, line 8: | change "$R_2$" to --$R^2$--. |
| Abstract, line 10: | change "$C_1 14C_4$" to --$C_1$-$C_4$--. |
| Column 2, line 2: | change "non-uniformity" to --nonuniformity--. |
| Column 2, line 25: | after "including" delete "," |
| Column 5, line 51: | change "wherein," to --wherein:--. |
| Column 7, line 3: | after "rendering" delete ",". |
| Column 8, line 26: | after "causing" delete ",". |
| Column 8, line 48: | change "$O_2$" to --$O_{12}$--. |
| Column 9, line 52: | after "$O_{20}$" delete "()". |
| Column 10, line 39: | change "scope:" to --scope.--. |
| Column 12, line 3: | after "containing" delete ",". |
| Column 13, line 17: | after "substrate" insert --,--. |

Signed and Sealed this

Tenth Day of April, 2001

Attest:

NICHOLAS P. GODICI

*Attesting Officer*     *Acting Director of the United States Patent and Trademark Office*